Figure 1:
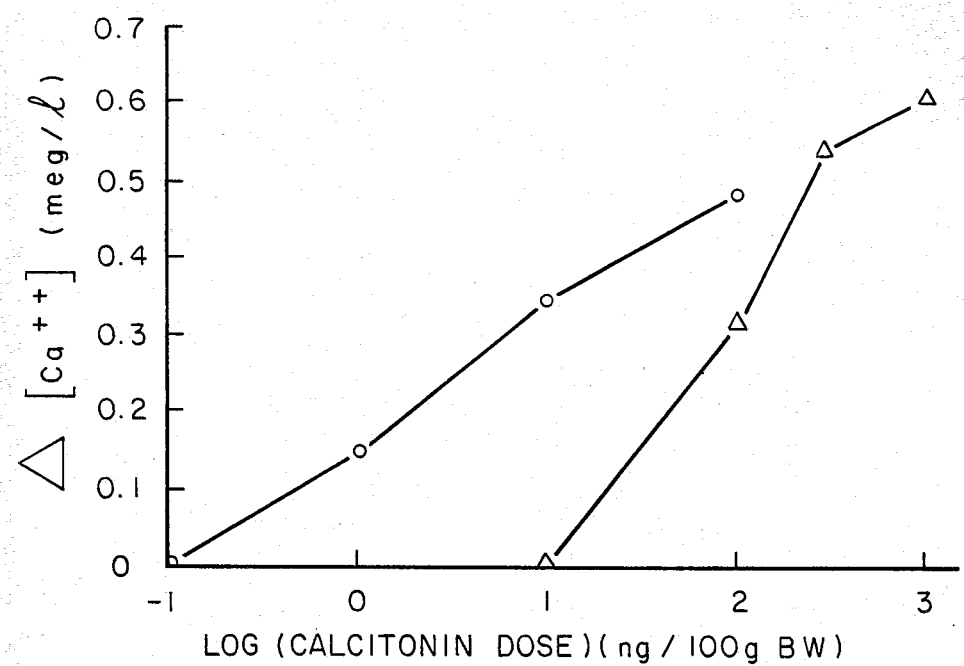

United States Patent [19]

Kaiser et al.

[11] Patent Number: 4,514,331
[45] Date of Patent: Apr. 30, 1985

[54] PEPTIDE HORMONES WITH CALCITONIN-LIKE ACTIVITY

[75] Inventors: Emil T. Kaiser; Gregory Moe, both of New York, N.Y.

[73] Assignee: University Patents, Inc., Westport, Conn.

[21] Appl. No.: 509,123

[22] Filed: Jun. 29, 1983

[51] Int. Cl.$^3$ ............................................ C07C 103/52
[52] U.S. Cl. ............................................ 260/112.5 T
[58] Field of Search ................................. 260/112.5 T

[56] References Cited

U.S. PATENT DOCUMENTS 4,086,221 4/1978 Sakakihara et al. ......... 260/112.5 T

OTHER PUBLICATIONS

*Calcitonin* 1980, Pecile ed., Excerpta Medica, Princeton, N.J., 1981, pp. 11–24.
Lehninger, *Biochemistry*, 2nd Ed., 1975, pp. 73–75.
Nakamuta et al., *Japan J. Pharmacol.* 31, 1981, pp. 53–60.
Morikawa et al., *Experientia*, vol. 32, No. 9, 1976, pp. 1104–1106.
Maier et al., *Clinical Endocrinology*, 5(Suppl.) 1976, pp. 327s–332s.
Yamashiro et al., *J. Am. Chem. Soc.*, vol. 100, 1974, pp. 5174–5179.
Pietta et al., *Chemical Communications*, 1970, pp. 650–651.

(List continued on next page.)

*Primary Examiner*—Delbert R. Phillips
*Assistant Examiner*—F. T. Moezie
*Attorney, Agent, or Firm*—Barbara A. Shimei

[57] ABSTRACT

Compounds of the formula:

$$\begin{array}{c} O \\ \| \\ -C-NH-R_2-Asn-Leu-Ser-Thr-HN-CH-C-NH- \\ | \qquad\qquad\qquad\qquad\qquad\qquad\quad | \\ \rule{1em}{0pt}R_1\rule{6em}{0pt} CH_2 \end{array}$$

wherein
$R_1$ is a moiety selected from the group consisting of $$H_2N-CH- \qquad \text{and} \quad CH_2- \\ \phantom{H_2N-}| \qquad\qquad\qquad\phantom{\text{and}\quad}| \\ CH_2-S-S- \qquad CH_2-CH_2-CH_2-$$

$R_2$–$R_{22}$ are amino acid moieties wherein
  $R_2$ is an optional moiety which when present is selected from the group consisting of Ser and Gly,
  $R_8$ is Leu, Val, or Ile,
  $R_{10}$ is Gln, Lys, or Gly,
  $R_{11}$, $R_{14}$, and $R_{20}$ are each independently selected from the group consisting of Gln and Lys,
  $R_{12}$ is Leu or Trp,
  $R_{13}$ is Gln or Ser
  $R_{17}$ is Gln or His,
  $R_{21}$ is Gln or Thr,
  $R_{22}$ is an optional moiety which when present is selected from the group consisting of Leu, Tyr, or Phe;
X comprises a series of eight amino acids each independently selected from the group consisting of Gly, Ser, Thr, Cys, Tyr, Asn, Gln, Asp, Glu, Lys, Arg, and His, with the proviso that not more than one of said eight amino acids may be selected from the group consisting of Asp, Glu, Lys, Arg, and His, and with the proviso that no four or more of said eight amino acids will spontaneously form helical, $\beta$-sheet, or $\beta$-turn conformations; and
$R_{23}$ is an amino acid amide selected from the group consisting of proline amide and glycine amide; the pharmaceutically acceptable salts thereof, compositions containing said compounds, and a method of lowering serum calcium levels using said compounds.

2 Claims, 2 Drawing Figures

OTHER PUBLICATIONS

MacIntyre et al., *Arthritis and Rheumatism*, vol. 23, No. 10, 1980, pp. 1139–1147.

Pollet et al., *J. Biol. Chem.*, vol. 254, No. 1, 1979, pp. 30–33.

Morrisett et al., *Biochemistry*, vol. 12, No. 7, 1973, pp. 1290–1299.

Hunter et al., *Nature*, vol. 194, 1962, pp. 495–496.

Edelstein et al., *J. Lipid Res.*, vol. 29, 1979, pp. 143–153.

Chou et al., *Ann. Rev. Biochem.*, vol. 245, No. 9, 1970, pp. 251–276.

Brewer et al., *J. Biol. Chem.*, vol. 245, No. 9, 1970, pp. 2402–2408.

*The Peptides*, vol. 2, Academic Press, N.Y., 1979, pp. 3–284.

*Proteins*, vol. 2, 3rd ed. Academic Press, N.Y., 1976, pp. 105–253.

Behrens et al., *Ann. Rev. Biochem.*, 38, 83–112 (1969).

Noda et al., *J. Biochem.*, 79, 353–359 (1976).

PEPTIDE HORMONES WITH CALCITONIN-LIKE ACTIVITY

The invention described herein was made in the course of work under a grant from the National Institutes of Health.

This invention relates to novel peptide hormones which exhibit calcitonin-like activity, to the pharmaceutically acceptable non-toxic salts thereof, to compositions containing said hormones, and to methods of lowering serum calcium levels by the administration of said hormones.

Calcitonin is a peptide hormone with a molecular weight of approximately 3,500 daltons which is produced by the parafollicular cells; these cells are scattered throughout the thyroid in mammals but in lower animals constitute a distinct organ, the ultimobranchial body. The hormone regulates serum calcium concentrations by opposing the bone and renal effects of parathyroid hormone and inhibiting bone resorption of calcium, resulting in hypocalcemia, hypophosphatemia, and decreased urinary calcium concentrations. Calcitonin is therefore used in the treatment of Paget's Disease, hyperparathyroidism, idiopathic hypercalcemia of infancy, osteolytic bone metastases, and to counteract the osteolytic effect of overdoses of vitamins A and D.

Calcitonins from at least seven different species, and the two isohormones of salmon calcitonin, have been sequenced and characterized biologically and a number of synthetic analogs have been studied, but few clear correlations between structure and function have been made. The common form of the hormone consists of 32 amino acids with a disulfide bridge between cysteine residues at positions 1 and 7 and prolinamide at the carboxy terminus. Otherwise the structures of the various calcitonins differ markedly from each other; human calcitonin differs from porcine calcitonin at 18 of the 32 residues. It is generally recognized that the cysteines at positions 1 and 7 taken together may be replaced by 2-aminooctanedioic acid, resulting in the analogous structure wherein the disulfide bridge of the cysteines has been replaced by an ethylene bridge. For a general review, see Behrens and Grinnan, Ann. Rev. Biochem. 38:83 (1969); Foster et al., "Calcitonin" in *Clinics in Endocrinology and Metabolism* [I. MacIntyre, ed.] (W. B. Saunders, Philadelphia, 1972) pp. 93–124.

Because of its therapeutic value, calcitonin is in great demand. Of the nine or more known calcitonins, only three, salmon, porcine, and human, are commercially available. Porcine calcitonin is isolated and purified at great expense from pork glands, whereas salmon and human calcitonin are primarily synthesized in vitro. Salmon calcitonin is the most active of the known calcitonins, and porcine is the most active known mammalian calcitonin. However, because foreign calcitonins tend to trigger an antigenic response and because human calcitonin is only weakly active there is a need for improved synthetic alternate peptide hormones with calcitonin-like activity. There is also a need to understand the elements required for activity so that these compounds can be modified to introduce desired pharmaceutical characteristics, such as increased half-life or oral activity, without losing efficacy.

It has now been discovered that compounds of the formula (I):

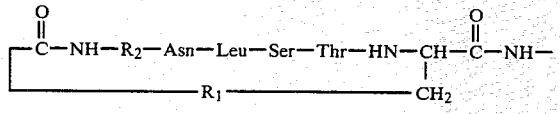

wherein
$R_1$ is a moiety selected from the group consisting of

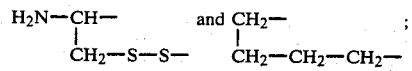

$R_2$–$R_{22}$ are amino acid moieties wherein
$R_2$ is an optional moiety which when present is selected from the group consisting of Ser and Gly,
$R_8$ is Leu, Val, or Ile,
$R_{10}$ is Gln, Lys, or Gly,
$R_{11}$, $R_{14}$, and $R_{20}$ are each independently selected from the group consisting of Gln and Lys,
$R_{12}$ is Leu or Trp,
$R_{13}$ is Gln or Ser,
$R_{17}$ is Gln or His,
$R_{21}$ is Gln or Thr,
$R_{22}$ is an optional moiety which when present is selected from the group consisting of Leu, Tyr, or Phe;
X comprises a series of eight amino acids each independently selected from the group consisting of Gly, Ser, Thr, Cys, Tyr, Asn, Gln, Asp, Glu, Lys, Arg, and His, with the proviso that not more than one of said eight amino acids may be selected from the group consisting of Asp, Glu, Lys, Arg, and His, and with the proviso that no four or more of said eight amino acids will spontaneously form helical, $\beta$-sheet, or $\beta$-turn configurations; and
$R_{23}$ is an amino acid amide selected from the group consisting of proline amide and glycine amide
have calcitonin-like activity in vivo. It has also been discovered that in addition to the 7-amino acid sequence at the amino end of the peptide with cysteine residues at positions 1 and 7 linked by a disulfide bridge (or with 2-aminooctanedioic acid replacing these two cysteines), which sequence can be designated as Section 1 of the peptide hormone, the following features are essential to activity:

(2) A 15-amino acid sequence at positions 8–22, which sequence spontaneously forms an amphiphilic helix characterized in that the hydrophilic amino acid residues are segregated along one side of the vertical axis of the helix while the hydrophobic amino acid residues are segregated along the opposite side of the vertical axis of the helix. Residues are considered hydrophobic if their hydrophobicity parameter as defined by Edelstein, C., F. J. Kezdy, A. M. Scanu and B. L. Shen, J. Lipid Res. 20:148 (1979), is greater than or equal to 0.5 and hydrophilic if the parameter is less than 0.5. The average $\alpha$-helicity parameter, $<P\alpha>$, as described by Chou, P. Y. and G. D. Fasman, Ann. Rev. Biochem. 47:251–76 (1978) must be greater than 1.03, and no more than half of the hydrophilic amino acid residues may be charged at pH 6.0–7.0.

(3) A 10-amino acid sequence at positions 23–32 (carboxy end of the peptide) having a proline residue at position 23 and an amino acid amide residue at position 32. These 10 amino acid residues are hydrophilic and no more than one may be charged at pH 6.0–7.0. They are selected to form a "random chain" so that no four or more of said 10 amino acids will spontaneously assume a helical, β-sheet, or β-turn configuration according to the empirical predictive parameters defined by Chou, P. Y. and G. D. Gasman, Ann. Rev. Biochem. 47:251–76 (1978).

These characteristics of the helix are more readily visualized when the compounds of the present invention are depicted in the following form:

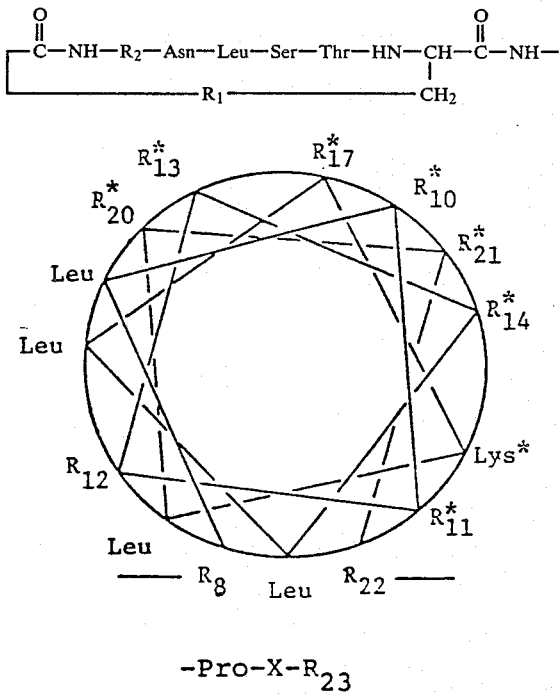

-Pro-X-$R_{23}$ wherein $R_1$, $R_{2-22}$, X, and $R_{23}$ are as previously defined. The hydrophilic amino acid residues in the helix are marked by an asterisk (*); the unmarked residues are hydrophobic. From this depiction it can easily be seen that the hydrophobic and hydrophilic residues are segregated on opposite sides of the helix. It is believed that this configuration is necessary for the interaction of the hormone with its specific receptor sites.

As used hereinabove and below, the three-letter abbreviations for the amino acid residues are those commonly used and accepted by persons in the peptide art; see, e.g., Lehninger, Albert L., Biochemistry, 2nd Ed. (Worth Publishers, Inc., New York, 1975), pp. 73–75. All amino acids and their derivatives are in the L-form.

Preferably, $R_8$ is Leu; $R_{10}$ is Gln or Lys; $R_{13}$, $R_{17}$, and $R_{21}$ are each Gln; and $R_{22}$ is an optional moiety which when present is selected from the group consisting of Leu and Tyr. Particularly preferred are compounds wherein $R_1$ is —S—S—. Most particularly preferred is the compound of the formula (II), which has been designated "MCT-I":

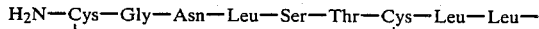
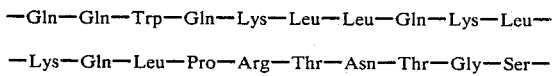

-continued

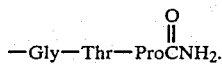

The basic amino acid residues (lysine, arginine, and histidine) of the compounds of Formula I may be in the form of their acid-addition salts. The hydrochloride, acetate, phosphate, citrate, fumarate, maleate, succinate, pamoate, and sulfate acid-addition salts are preferred. Particularly preferred are the acetate and hydrochloride salts. It is to be understood that for the purposes of this invention, the acid-addition salts of the hormone of Formula I are equivalent to the parent free peptide.

The compounds of Formula I may be synthesized by methods well-known to those skilled in the art of peptide synthesis, e.g. solution phase synthesis (see Finn, F. M. and K. Hofmann, in Proteins, Vol. 2, 3rd Ed., H. Neurath and R. L. Hill, eds. (Academic Press, New York, 1976), pp 105–253), or solid phase synthesis (see Barany, G. and R. B. Merrifield, in The Peptides, Vol. 2, E. Gross and J. Meienhofer, eds. (Academic Press, New York, 1979) pp. 3–284). Preferably these compounds are synthesized by the solid phase method on a benzhydrylamine-substituted polystyrene resin crosslinked with 1% divinylbenzene, see Pietta, P. G. and G. R. Marshall, J. Chem. Soc. D: 650–651 (1970). The α-amino group of the carboxy-terminal amino acid ($AA_{32}$) is first shielded with a selectively cleavable N-Terminal protecting group. Preferably, this group is t-butoxycarbonyl (Boc). Amino acids with the $N^\alpha$-Boc shielding group in place are commercially available from Bachem Inc., Marina Del Rey, Calif. The blocked amino acid ($N^\alpha$-Boc-$AA_{32}$) is then coupled to the resin using N-hydroxybenzotriazole (HOBt) in conjunction with dicyclohexylcarbodiimide (DCC) as condensing agents. The $N^\alpha$-Boc group is subsequently removed by treatment with a strong anhydrous organic acid, preferably trifluoroacetic acid neat or about 25–75% (50% preferred) in methylene chloride, at about 20°–30° C. for about 30–60 minutes. The reaction mixture is then neutralized with a hindered organic base, e.g. diisopropylethylamine or N-methylmorpholine, preferably about 2–10% diisopropylethylamine in methylene chloride at about 20°–30° C. for about 2–6 minutes. The amino acid of position 31 ($AA_{31}$) is then added to the N-terminal amine of $AA_{32}$ by reaction with the symmetric anhydride or active ester of $N^\alpha$-Boc-$AA_{31}$ in the presence of methylene chloride at about 20°–30° C. for about 20–60 minutes, followed by removal of the $N^\alpha$-Boc blocking group of $AA_{31}$ by treatment with about 25–75% (50% preferred) trifluoroacetic acid in methylene chloride at about 20°–30° C. for about 30–60 minutes. In a similar manner, the remaining amino acid residues are added in sequence and the peptide chain is built up from the C-terminal end. See Yamashiro, D. and C. H. Li, J. Am. Chem. Soc. 100:5174 (1978).

If $R_1$ is to be

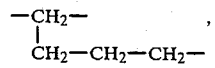

the C-2 amino group and the C-8 carboxyl group of 2-aminooctanedioic acid are first protected; when the growing peptide chain has reached the point where $AA_8$ ($R_8$) is in position, the C-1 carboxy on the shielded 2-aminooctanedioic acid is bonded to the α-amine moiety of AA$_8$. The α-carboxyl group of AA$_6$ is then added to the C-2 amine of the 2-aminooctanedioic acid; AA$_5$ is added to AA$_6$, and so on through AA$_2$. The C-8 carboxyl group on the 2-aminooctanedioic acid is then deprotected to allow it to react with the α-amino moiety of AA$_2$. Thus the two halves of 2-aminooctanedioic acid each function as a separate amino acid at positions 1 and 7, linked through an ethylene bridge. For details on methods of incorporating 2-aminooctanedioic acid in the proper positions, see Morikawa, T. et al., *Experientia* 32:1104–1106 (1976).

It is understood by those skilled in the art that certain amino acids contain reactive side groups which must be shielded during the coupling reaction. Thus the N-guanidinium moiety of N$^\alpha$-BocArg is tosylated to yield N$^\alpha$-BocArg(N$^g$-Tos). The thiol group of N$^\alpha$-BocCys is protected by a 4-methoxybenzyl moiety to yield N$^\alpha$-BocCys(S-4-MeO-Bzl). N$^\alpha$-Boc-Lys is converted to N$^\alpha$-BocLys(N$^\epsilon$-2-ClZ) wherein the α-amino of lysine is protected by a 2-chlorobenzyloxycarbonyl moiety. N$^\alpha$-BocSer(OBzl) and N$^\alpha$-BocThr(OBzl) are formed from N$^\alpha$-BocSer and N$^\alpha$-BocThr, respectively; the hydroxy groups of serine and threonine are converted to an ether linkage with the benzyl moiety. The indole nitrogen of N$^\alpha$-BocTrp is formylated for protection to yield N$^\alpha$-BocTrp(N$^{in}$-For). These shielded amino acids may be prepared according to methods given in Barany, G. and R. B. Merrifield, in *The Peptides*, Vol. 2, E. Gross and J. Meienhofer, eds. (Academic Press, New York, 1979) pp. 169–250, or they may be obtained commercially from Bachem Inc., Marina Del Rey, Calif.

The shielded amino acid residues are converted to their symmetrical anhydrides by reaction with dicyclohexylcarbodiimide in methylene chloride in a ratio of 2 molar equivalents of amino acid per molar equivalent of DCC at about 5°–10° C. for about 15 minutes. The resulting product is suitable for use without further isolation and purification. Alternatively, the shielded amino acids are converted to their active esters by reaction with HOBt and DCC in a ratio of 1:1:1 molar equivalents.

The completed peptide is cleaved from the resin with simultaneous removal of all protecting groups except the N$^{in}$-formyl by treatment with anhydrous liquid hydrofluoric acid:anisole (7-9:1, v/v) at 0° C. for about 30–60 min. One of the advantages of the benzhydrylamine-substituted polystyrene resin used is that the carboxy-terminal amino acid residue (AA$_{32}$) is spontaneously yielded in its amino acid amide form upon cleavage. Crude peptide is removed from the resin by washing with 5–20% acetic acid. Ten percent acetic acid is preferred.

The crude peptide is then preferably lyophilized. During synthesis, the cysteine residues may have oxidized. The thiol groups are reduced to their free form by treatment with a reducing agent such as excess dithiothreitol or β-mercaptoethanol in a mild physiological buffer such as sodium phosphate or carbonate, tris, MOPS, etc. 0.05M sodium phosphate, pH 7.0, is preferred.

If R$_1$ is to be

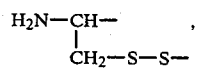

the peptide solution is diluted in the same buffer as above to a volume of about 5 liters and a solution of 0.02M K$_3$Fe(CN)$_6$ (oxidizing agent) is added slowly with stirring at 20°–30° C. to induce the formation of the disulfide bridge between the cysteine residues at positions 1 and 7.

The peptide is then concentrated and purified by procedures well-known to those skilled in the art, e.g. by molecular sieving, ion exchange chromatography, HPLC, evaporation, lyophilization, etc., and the N$^{in}$-formyl group is removed. Preferably, the peptide is concentrated and purified by absorption on an ion exchange column such as CM-Sephadex C-25$^{(R)}$ (Pharmacia Fine Chemicals, Piscataway, N.J.), followed by elution with a linear salt gradient, e.g. 0.0 to 0.3M NaCl in the same buffer used to form the bridge moiety. The peptide elutes in about 2.8M NaCl and is further purified by HPLC using a linear gradient of from about 20–50% acetonitrile 50% in 0.2M sodium phosphate buffer, pH 2.5. The resulting solution is desalted and the N$^{in}$-formyl protecting group is removed quantitatively by treatment with a nucleophilic species in aqueous solution, e.g. piperidine sodium hydroxide or hydrazine, preferably 0.5M aqueous piperidine, at 0° C. for about 20 minutes. The deprotective reaction is terminated by addition of acid, preferably acetic acid. Alternatively, the N$^{in}$-formyl group may be removed by methods given in Barany, G. and R. B. Merrifield, in *The Peptides*, Vol. 2, E. Gross and J. Meienhofer, eds. (Academic Press, New York, 1979) p. 220. The peptide is then once again purified by HPLC, eluting with about 35% acetonitrile in 0.2M sodium phosphate buffer, pH 2.5.

The acid-addition salts of the basic amino acid residues are prepared by treatment of the peptide with the appropriate organic or inorganic acid according to procedures well-known to those skilled in the art; or the desired salt may be obtained directly by lyophilization out of the appropriate acid.

The compounds of formula I are useful to lower the serum plasma calcium level in warm-blooded animals suffering from elevated serum plasma calcium levels when administered in amounts ranging from about 0.1 ng. to about 10 ng. per kg. of body weight per day. A preferred dosage range for optimal results would be from about 0.15 ng. to about 8 ng. per kg. of body weight per day, and such dosage units are employed so that a total of from about 0.1 mg. to about 0.56 mg. of the active compound for a subject of about 70 kg. of body weight are administered in a 24-hour period. This dosage regimen may be adapted to provide the optimum therapeutic response. For example, several divided doses may be administered daily, or the dose may be proportionally reduced as indicated by the exigencies of the therapeutic situation. The compound may be administered in the form of the free peptide or as a non-toxic pharmaceutically acceptable salt thereof. The term "pharmaceutically acceptable salt" refers to those acid-addition salts of the parent compound which do not significantly adversely affect the pharmaceutical properties (e.g. toxicity, effectiveness etc.) of the parent compound, such as are conventionally used in the pharmaceutical art.

The active compounds may be administered parenterally, e.g. by subcutaneous, intramuscular, or intravenous injection. Solutions or suspensions of these active compounds as a pharmaceutically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms. The peptide hormones of the present invention have a natural tendency to adhere to glass; therefore these preparations preferably also contain a pharmaceutically acceptable protein such as gelatin or albumin to competitively inhibit this effect.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, polyol (e.g., glycerol, propylene glycol and liquid polyethylene glycol), and suitable mixtures thereof. Compositions suitable for intramuscular or subcutaneous injection may also contain minor amounts of salts, acids, and bases to adjust tonicity and buffer the pH. Suitable pharmaceutically acceptable buffering and tonicity agents are readily determinable by persons skilled in the art.

A further understanding of this invention may be had from the following non-limiting examples. As used hereinabove and below unless expressly stated to the contrary, all temperatures and temperature ranges refer to the centigrade system and the terms ambient or room temperature refer to about 20° C. The term percent or (%) refers to weight percent and the terms mole and moles refer to gram moles.

EXAMPLE 1

Synthesis of MCT-I

MCT-I was synthesized by the solid phase method using a benzhydrylamine-substituted polystyrene resin crosslinked with 1% divinylbenzene. The C-terminal amino acid BocPro was coupled to the resin using N-hydroxybenzotriazole (HOBt) and dicyclohexylcarbodiimide (DCC). Thereafter, symmetric anhydrides of BocArg (N$^g$-Tos), BocCys(S-4-MeO-Bzl), BocGly, BocLeu, BocLys(N$^\epsilon$-2-ClZ), BocPro, BocSer(OBzl), BocThr(OBzl), and BocTrp(N$^{in}$-For) and a deprotection and coupling program similar to that employed by Yamashiro, D. and C. H. Li, *J. Am. Chem. Soc.* 100:5174 (1978) was used, except for BocAsn, which was coupled by the HOBt/DCC method. Cleavage from the resin and removal of all the remaining protecting groups, except for the N$^{in}$-formyl, were accomplished by treatment with anhydrous liquid HF in the presence of anisole (7:1, v/v) at 0° C. for 45 min. Crude peptide was removed from the resin by washing with 10% acetic acid. The residue remaining after lyophilization was treated with excess dithiothreitol in 0.05M sodium phosphate buffer at pH 7.0. The intramolecular disulfide bond between cysteine residues 1 and 7 was formed by diluting the peptide solution to a volume of 5 liters in the same buffer and adding a solution of 0.02M $K_3Fe(CH)_6$ slowly with stirring. The resultant dilute peptide solution was concentrated by passing it through a CM-Sephadex C-25 column, followed by a linear gradient of NaCl from 0.0 to 0.3M employing the same buffer. Fractions from this column were purified further by loading them directly onto a Waters ™ $C_{18}$ semi-preparative HPLC column and then eluting with a linear gradient of $CH_3CN$ from 20% to 50% in 0.2M sodium phosphate buffer, pH 2.5. After desalting the resultant solution, the N$^{in}$-formyl protecting group was removed quantitatively by treatment with 0.5M aqueous piperidine at 0° C. for 20 minutes. The deprotective reaction was terminated by the addition of acetic acid. Final purification was carried out by loading the reaction mixture directly onto the Waters $C_{18}$ semi-preparative column and eluting with 35% $CH_3CN$ in the same buffer. The yield of purified MCT-I after a final desalting step and lyophilization was 10% based on the original substitution level of BocPro. The peptide was judged to be pure based on the observation at 230 nm of a single peak when the peptide was eluted from a Waters $C_{18}$ reversed phase column using a gradient from 20% to 50% $CH_3CN$ as the eluting solvent and from its amino acid analysis after hydrolysis with 5.5M HCl.

Amino Acid Analysis: Arg 1.1 (1), Asp 2.01 (2), Cys 2.09 (2), Glu 5.00 (5), Gly 3.02 (3), Leu 7.14 (7), Lys 2.94 (3), Pro 1.63 (2), Ser 1.61 (2), Thr 3.5 (4).

EXAMPLE 2

Characterization of MCT-I

The circular dichroism (CD) spectra of MCT-I and salmon calcitonin (designated "SCT-I", available from Armour Pharmaceuticals, Kankakee, Ill.) from 250 nm to 205 nm show minima at 222 nm and 208 nm characteristic of α-helical structure. For MCT-I, the mean residue molar ellipticity at 222 nm, $[\theta]_{222}$, was $-7,800$ deg $cm^2$/dmol ($10^{-4}$M peptide, 0.02M sodium phosphate buffer, 0.16M KCl, pH 7.4), from which the α-helicity was estimated to be 30% according to the method of Morrisett, J. D., J. S. K. Davis, H. J. Pownall, and A. M. Gotto, *Biochemistry* 12:1290 (1973). The value of $[\theta]_{222}$ does not change over a range of concentration of MCT-1 from $10^{-7}$M to $10^{-4}$M, provided that binding to glass is prevented by pretreatment of the spectrometer cell with polyethylene glycol (MW 15K–20K). This suggests strongly that MCT-I remains monomeric over the concentration range employed, a conclusion supported by the measurement of a molecular weight of about 4,500 at a concentration of $10^{-4}$M MCT-I by means of ultracentrifugation using a Beckman Spinco Airfuge according to the procedure of Pollet, R. J., B. A. Haase, and M. L. Standaert, *J. Biol. Chem.* 254:30 (1979). Similarly, the value of $[\theta]_{222}$ for solutions of SCT-I over the same concentration range and under the same conditions also remains constant at $-4,600$ deg $cm^2$/dmol, leading to an estimate of 20% α-helix for this peptide. In 50% trifluoroethanol, a structure promoting solvent, both MCT-I and SCT-I were estimated to be 50% α-helical at a concentration of $5 \times 10^{-5}$M, as was found by Brewer, H. D. and H. Edelhoch, *J. Biol. Chem.* 245:2402 (1970) for porcine calcitonin (PCT) in 50% 2-chloroethanol.

At the air-water interface, MCT-I and SCT-I form insoluble monolayers when spread from concentrated solutions in 0.01M HCl. The force-area ($\pi - A$) curves between 5 and 12 dyn/cm are described by the equation $\pi[A - A_\infty(1 - \kappa\pi)] = nRT$ where $\kappa$ is the compressibility and $A_\infty$ is the limiting molecular area extrapolated to zero surface pressure. The parameters calculated for the two peptides were very similar, $\kappa = 0.016$ cm/dyn for MCT-I and 0.02 cm/dyn for SCT-I, while $A_\infty = 362$ Å$^2$ for MCT-I and $A_\infty = 322$ Å$^2$, for SCT I. However, the collapse pressure of 24 dyn/cm found for the monolayer of MCT-I was much higher than the value of 14 dyn/cm observed for SCT-I.

EXAMPLE 3

In vitro Activity

In order to study the receptor binding properties of MCT-I and SCT-I, $^{125}$I-SCT-I was prepared by the method of Hunter, W. M. and F. C. Greenwood, *Nature* 194:495 (1962). The iodinated hormone was purified by ion exchange chromatography on SP-Sephadex C-25 TM (Pharmacia Fine Chemicals, Piscataway, N.J.). The unreacted labelling material was first washed from the column with 0.01M Tris-HCl, 0.1% bovine serum albumin (BSA), pH 7.4 buffer, followed by elution of the monoiodinated SCT-I with 0.2M NaCl at pH 8 in the same buffer. Fractions from the single symmetrical peak which was eluted with this buffer were combined, adjusted to pH 7.5, and frozen in small aliquots until needed. The specific activity of the radioiodinated peptide was ~160 µCi/µg. Competitive binding experiments with rat brain homogenates were carried out as described by Nakamuta H., S. Furukawa, M. Koida, H. Yajima, R. C. Orlowski, and R. Schlueter, Japan *J. Pharmacol.* 31:53 (1981). This method has been shown to given binding curves for calcitonin analogues comparable to the more commonly used kidney binding assay, see S. J. Marx, C. J. Woodward, and G. D. Auerbach, *Science* 178:999 (1972), and the brain tissue is more convenient to prepare and use. The results are shown in FIG. 1, competitive inhibition of $^{125}$I-SCT-I binding to brain particulate fraction by SCT-I (O) and MCT-I (Δ). Each point represents the mean of three triplicate determinations. The binding curves obtained gave IC$_{50}$ values for SCT-I of about 2.5 nM, in agreement with the value reported earlier by Nakamura et al., supra, and 17 nM, for MCT-I which compares with the value of 17 nM found for PCT (Ibid.)

EXAMPLE 4

In vivo Activity

Figure 2:
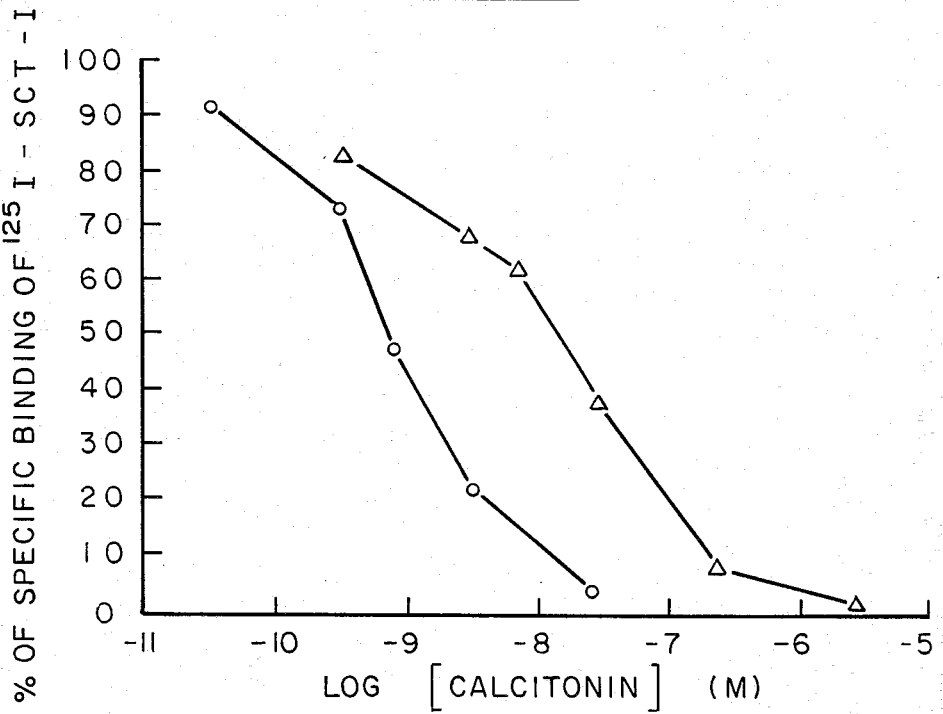

To assess the biological potency of MCT-I in vivo, 20 male Sprague-Dawley rats, 3-4 weeks old, were given subcutaneous injections (0.15 ml/100 g body weight) of SCT-I or MCT-I in 0.9% saline, 0.1% BSA, pH 4.5 in graded doses or, alternatively, of saline solution alone. Blood was withdrawn 1 hour after the injections, and the calcium concentration in the plasma determined by atomic absorption spectroscopy. The dose-response curve in FIG. 2 summarizes the results for SCT-I (O) and MCT-I (Δ). Each point represents the difference between the average serum Ca$^{+2}$ concentration for rats given only saline and the average for those given a particular dose of either MCT-I (15 rats per point) or SCT-I (5 rats per point). As with the binding studies, MCT-I is about 10-fold less potent than SCT-I, or approximately as active as PCT, the most potent mammalian analog.

Although the sequence of amino acids in MCT-I differs from that in SCT-I from positions 8 to 22, the MCT-I reproduced all of the chemical and biological properties of the salmon calcitonin that were examined. Like SCT-I, MCT-I was monomeric in aqueous solution. MCT-I showed somewhat more α-helical character than the salmon calcitonin did under these conditions, and at the air-water interface, an amphiphilic environment, it formed a much more stable monolayer than did SCT-I. Moreover, MCT-I displaced a specifically bound ligand from calcitonin receptors in vitro and effected a potent hypocalcemic response in the rat bioassay. Taken together, these results provide strong evidence that the region from residues 8 to 22 of the calcitonins has a primarily structural role, interacting in the amphiphilic α-helical form with the amphiphilic environment of the calcitonin receptor.

We claim:

1. The compound of the formula:

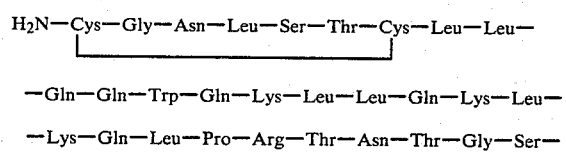

H$_2$N—Cys—Gly—Asn—Leu—Ser—Thr—Cys—Leu—Leu—

—Gln—Gln—Trp—Gln—Lys—Leu—Leu—Gln—Lys—Leu—

—Lys—Gln—Leu—Pro—Arg—Thr—Asn—Thr—Gly—Ser—

—Gly—Thr—ProCNH$_2$ (with C=O)

and the pharmaceutically acceptable salts thereof.

2. A method of lowering serum plasma calcium levels in warm-blooded animals comprising administering to said warm-blooded animal a serum plasma calcium-lowering effective amount of a compound according to claim 1.

* * * * *

UNITED STATES PATENT AND TRADEMARK OFFICE
CERTIFICATE OF CORRECTION

PATENT NO. : 4,514,331  
DATED : Apr. 30, 1985  
INVENTOR(S) : Emil T. Kaiser and Gregory R. Moe It is certified that error appears in the above—identified patent and that said Letters Patent is hereby corrected as shown below:

In the Abstract, after "compounds of the formula", delete:

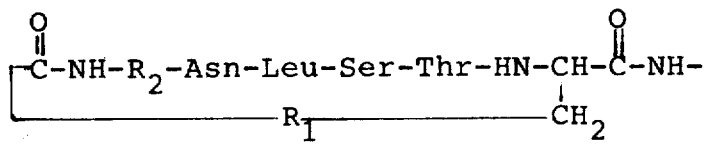

and insert:

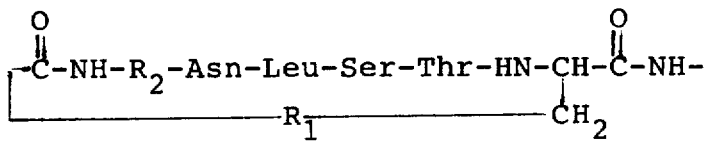

$-R_8-Leu-R_{10}-R_{11}-R_{12}-R_{13}-R_{14}-Leu-Leu-R_{17}-Lys-Leu-$
$-R_{20}-R_{21}-R_{22}-Pro-X-R_{23}$

UNITED STATES PATENT AND TRADEMARK OFFICE
CERTIFICATE OF CORRECTION

PATENT NO. : 4,514,331
DATED : Apr. 30, 1985
INVENTOR(S) : Emil T. Kaiser and Gregory R. Moe It is certified that error appears in the above—identified patent and that said Letters Patent is hereby corrected as shown below:

In the Abstract, delete "$R_{22}$ is an optional moiety which when present is selected from the group consisting of Leu, Tyr, or Phe;" and insert -- $R_{22}$ is an optional moiety which when present is selected from the group consisting of Leu, Tyr, and Phe; --.

Column 2, lines 1-6, delete:

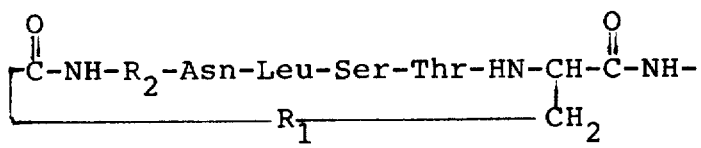

and insert:

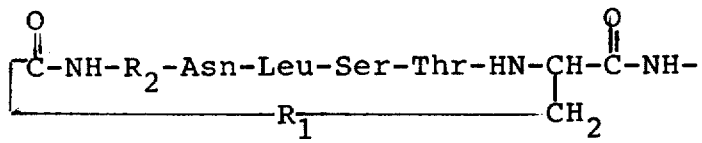

$-R_8-Leu-R_{10}-R_{11}-R_{12}-R_{13}-R_{14}-Leu-Leu-R_{17}-Lys-Leu-$
$-R_{20}-R_{21}-R_{22}-Pro-X-R_{23}$

UNITED STATES PATENT AND TRADEMARK OFFICE
CERTIFICATE OF CORRECTION

PATENT NO. : 4,514,331

DATED : Apr. 30, 1985

INVENTOR(S) : Emil T. Kaiser and Gregory R. Moe

It is certified that error appears in the above—identified patent and that said Letters Patent is hereby corrected as shown below:

Column 2, lines 27-28: Delete "Leu, Tyr, or Phe;" and insert -- Leu, Tyr, and Phe; --.

Column 7, line 63: Delete "$K_3Fe(CH)_6$" and insert -- $K_3Fe(CN)_6$ --.

Column 8, line 6: Delete "deprotective" and insert -- deprotection --.

Column 9, line 30: Delete "FIG. 1" and insert -- FIG. 2 --.

Column 10, line 2: Delete "FIG. 2" and insert -- FIG. 1 --.

Signed and Sealed this

Twenty-fifth Day of March 1986

[SEAL]

Attest:

DONALD J. QUIGG

Attesting Officer  Commissioner of Patents and Trademarks